United States Patent [19]

Tarabishi

[11] Patent Number: 4,812,315

[45] Date of Patent: Mar. 14, 1989

[54] DIET PILLS

[76] Inventor: M. Hisham Tarabishi, P.O. 12901, Upper St. Clair, Pa. 15241

[21] Appl. No.: 49,542

[22] Filed: May 14, 1987

[51] Int. Cl.$^4$ .............................................. A61K 9/46
[52] U.S. Cl. ..................................... 424/466; 424/44; 206/828; 426/658; 426/804
[58] Field of Search ................ 424/464, 466, 443, 44; 206/828; 426/658, 804

[56] References Cited

U.S. PATENT DOCUMENTS

| | | | |
|---|---|---|---|
| 3,082,091 | 3/1963 | Smith | 424/466 X |
| 4,184,888 | 1/1980 | Zoumut | 106/128 |
| 4,401,682 | 8/1983 | Battista | 426/656 X |
| 4,678,661 | 7/1987 | Gergely et al. | 424/466 X |

FOREIGN PATENT DOCUMENTS 2538789  7/1984  France ................................ 206/828

*Primary Examiner*—Michael Lusignan
*Attorney, Agent, or Firm*—William J. Ruano

[57] ABSTRACT

A diet pill in the form of a sealed container of cellulose material containing a gas producing powder, such as sodium bicarbonate which expands the pill in volume as the result of reaction with gastric juice and liquid in the user's stomach. Such expansion gives a sense of fullness of the stomach. The pill may also contain a fiber, such as psyllium hydrophillic mucilloid, which swells in the user's stomach. The pill may be tubular and sealed by end ties of silk or catgut or other digestible or indigestible material. The tubular pill may be compacted in size by folding several times or collapsing in accordion fashion to enable swallowing.

12 Claims, No Drawings

DIET PILLS

This invention relates to diet pills taken orally and that swell upon reaching the stomach to curb the appetite and provide other beneficial effects.

BACKGROUND OF THE INVENTION

The most common type of diet pills presently on the market are as follows:

PILLS THAT SUPPRESS THE APPETITE

These have the possibility of side effects on the central nervous system and the rest of the body systems, in addition to the side effect of constipation.

FIBER DIET PILLS

These are not effective to maintain the diet as well as curb the appetite adequately, since they leave the stomach in a relatively short time.

STOMACH BALLOONS

These require surgical procedures with the risk of any surgical procedure, beside the fact there is a fatal complication reported as a result of rupture. Once it is inserted, it has a fixed size and fixed residual volume in the stomach and cannot be altered without another surgical removal and re-application. Constipation also can be a result of low volume intake.

NASAL INHALANTS

These are newly reported in medical journals. It is too early to determine its side effects, but it can be reasonably assumed it will be accompanied with constipation, because of low volume intake which results in low residue, which is essential for normal bowel movements. Other potential problems will be localized in the area of nasal and upper respiratory side effects and limitations.

SUMMARY OF THE INVENTION

An object of the present invention is to provide a novel diet pill that will overcome the above-named disadvantages of existing diet pills.

Briefly, the invention comprises a cellophane dialysis tubing or similar tubing which is provided with an inner coating of powder or granules, such as psyllium hydrophillic mucilloid and sodium bicarbonate powder. The tubing is closed and folded or collapsed into very compact size to enable it to be taken orally. Upon reaching the stomach, the tubing expands as a consequence of contacting the liquid of the stomach so as to occupy a greater volume of the stomach as the result of gas formed by the sodium bicarbonate powder.

The main elements that contribute to the sense of hunger and physiology of it are: empty stomach and gastric juice including hydrochloric acid; meal time; habit, sense of smell; and sense of taste.

DETAILED DESCRIPTION OF A PREFERRED EMBODIMENT

The ingredient and material for fabricating pills of the present invention are:

The cellophane dialysis tubing; psyllium hydrophillic mucilloid granules or powder; sodium bicarbonate powder; and surgical ties material: silk or any absorbable surgical ties like catgut. Another possible alternative for dialysis tubing is sheets of cellophane.

The dialysis tubing is basically cellulose which is a natural product in vegetation and processed in chemo physiological steps to manufacture the dialysis tube, which is used widely in medicine for dialysis. It has a property of permeability to fluid and gases and also swells moderately with water application and increases its flexibility. Generally it is an inert material.

Psyllium hydrophillic mucilloid is a natural fiber containing no chemical stimulants. It swells by absorbing water and produces volume much larger than when in dry form. It is also inexpensive.

Sodium bicarbonate is the only chemical product which is widely used over the counter as anti-acids and is widely used in food products and other medical applications. It is alkline. When hydrochloric acid is added, as for example in stomach juice, it produces carbon dioxide gas and sodium chloride salt and water. All are normal physiological substances.

Surgical tie materials like silk is a neutral substance or catgut is also used as surgical ties, or any digestible or indigestible tie.

Cellophane sheets can be used instead of dialysis tubing and can be of a diameter of $1\frac{1}{2}$ cm with $1\frac{1}{2}$ to 2 turns. The rest of the process is the same and the folding would be accordion-style.

Another alternative is to leave the tubing with no ties. It would allow escape of the contents, but with mild compromising of the effectiveness.

In the manufacture of the pill, dialysis tubing of cellophane is washed to remove any impurities, such as sulfur and glycerine. The dialysis tube is moistened with water and moist air is blown from one end of the tube to open it. High humidity air is blown from one collapsed end with the mixture of psyllium hydrophillic mucilloid and sodium bicarbonate in about equal amounts, by weight. Particles of this mixture will adhere to the inside tube diffusely. The tube then is vacuumed mildly to allow collapse of its walls and upon removing the air from the tube, the tube will then become flat. Separate surgical ties are to be applied at each end of the tube about a distance of 5–6 cm. apart. Such tubes may be more easily manufactured by using a long tube and applying double ties at 5 or 6 cm apart. Cutting of the tube then is performed between the double ties, producing a plurality of tubes of about 5 cm in length. The size of the ties used will be four zeros to three zeros as was found the most practical and easier to handle.

Each prepared tube can be folded in different ways such as wrapping or folding or any other compact shape and be compressed to take the form of either oval or cylinder shape to enable easy swallowing. This must not be done in completely dry air, but has to be done with humidity. Each pill can be sprayed outside with a thin layer of coating like gelatin to maintain its small shape or placed in capsules or cachets of substance that meet the criteria of oral intake and be readily dissolvable in the stomach. The finished pills may be used as follows: $\frac{1}{2}$ hour to 15 minutes before regular meal, average 4–5 pills are taken orally with one glass of water or more if needed. The surface of the pills will start imbibing and absorbing the water surrounding them as well as some of the gastric juice, which contains natural hydrochloric acid. A slow reaction will start between the hydrochloric acid and small amount of sodium bicarbonate to produce just enough carbon dioxide gas to slowly expand the tube and inflate it, while traces of sodium chloride salt and water are also an end result of the process.

By inflating the tubes, they will occupy reasonable space of the stomach, which satisfies the feeling of fullness in the stomach but also neutralizes some of the acid base in the gastric juice, which is the hydrochloric acid. Both together will reduce significantly the sense of hunger pain. In the mean time the psyllium hydrophillic mucilloid granules also slowly start to swell by osmosis. By the time the carbon dioxide gas starts to escape and dissolve from the tubing, the psyllium hydrophillic mucilloid granules swell enough to compensate partially for the deflated tube. But meanwhile it has adequate size much larger than the original pill.

In about an average period of three hours the tubes will start passing to the small intestines due to normal physiological gastrointestinal function and since the tubing surface is very slippery and the size of it is reasonably small, as well as very flexible the process of passing through the entire small and large intestines will go naturally while the psyllium hydrophillic mucilloid granules slowly keep gaining more water content by osmosis and trap the water in the tube, which will give the tube its bulky size, stimulating normal, healthy bowel movements. The process takes an average of 8-36 hours, depending on personal habit. This would give extra advantage to these pills as to eliminate problems with functional constipation. The tubes pass with the stools smoothly. At this time the tubes are discolored, depending on the stool contents. Some times the discoloration comes from whatever the food intake consists of, especially red colored material, for example having the color of beets, etc.

The pill of the present invention is recommended for age 18 years to middle age, unless medically unadvised due to upper GI or lower GI abnormalities or pathology. In these instances upper GI and lower GI series would be recommended. It is not recommended with any symptoms of dysphagia or difficulty swallowing. Organic constipation should be excluded by the physician before starting the pills. Organic obesity, for example hormonal obesity, should be excluded as this method is only recommended for physiologically overweight individuals. Individuals who are on salt restrictions should be aware of the mild sodium chloride release in the body. Outstanding advantages of the pill of the present invention are that it takes care of the problem of small volume intake but providing bulk essential for bowl movement and to suppress the appetite. In other words it satisfies the sense of fullness, physiologically volume wise. It neutralizes some of the hydrochloric acid contents of the gastric juice, which adds in its effectiveness to reduce the hunger pain. It keeps intact the sense of smell and taste and with enjoyment of regular meals with no restriction of diet since it only reduces the stomach capacity to accomplish full meal satisfaction with a smaller amount of intake, but with some quality of the individual's regular meal. It has the flexibility in adjusting the stomach capacity for each individual by taking more or less pills to satisfy the need, as long as it does not exceed the recommended dosage. It eliminates the fixed volume or space which accompanies the surgical stomach balloon placement. As it gives the individual the flexibility of decreasing the number of pills in certain situations or occasions: it solves the problem of physiological constipation accompanied with many diet pills. All materials or substances are either natural or over the counter products. It eliminates the wide range of side effects of the pharmaceutical diet pills or appetite suppressants. It maintains regular diet with no restrictions other than reducing the food intake.

While cellophane dialysis tubing is preferred, other cellulose material which dissolves and slightly swells upon swallowing, particularly natural cellulose material, may be used instead. While sodium bicarbonate is preferred, other material which produces gas as the result of contacting gastric juice and liquid in the user's stomach may be used instead. While psyllium hydrophillic mucilloid is preferred, other natural fibers which swell by absorbing water to produce a much larger volume than when in dry form may be used instead.

While I have illustrated and described several embodiments of my invention, it will be understood that these are by way of illustration only and that various changes and modifications may be contemplated in my invention and within the scope of the following claims:

I claim:

1. A diet pill comprising a very compactly folded sealed package of cellulose dialysis tubing material containing a material which produces gas and expands in size by unfolding to occupy a larger volume in the stomach and gives the feeling of fullness as the result of reaction with gastric joice and liquid in the user's stomach upon swallowing the pill.

2. A pill as recited in claim 1 wherein said package also includes a fiber which swells by absorbing water.

3. A pill as recited in claim 2 wherein said gas producing material is sodium bicarbonate.

4. A pill as recited in claim 2 wherein said fiber is psyllium hydrophillic mucilloid.

5. A pill as recited in claim 2 wherein said cellulose material is natural cellulose which absorbs and swells by contacting liquid.

6. A pill as recited in claim 2 wherein said package is cellophane tubing having both ends tied separately and tightly enough to seal both ends of the tubing.

7. A pill as recited in claim 6 wherein said tubing is collapsed in accordion fashion into a compact size suitable for swallowing.

8. A pill as recited in claim 6 weherein said tubing is folded several times into a sufficiently small package as to be swallowed.

9. A pill in the form of a compactly folded, sealed natural cellulose tube which has adhered to its inner walls sodium bicarbonate and psyllium hydrophillic mucilloid to enable the tube to expand in size when swallowed as the result of formation of gas by said sodium bicarbonate.

10. A pill as recited in claim 9 which is compacted in size by folding several times.

11. A pill as recited in claim 6 having ties of digestible material.

12. Pill as recited in claim 6 having ties of non-digestible material.

* * * * *